United States Patent [19]

Farooq et al.

[11] Patent Number: 4,782,087
[45] Date of Patent: Nov. 1, 1988

[54] INSECTICIDAL PROP-1-YNYL-3-PHENOXYBENZYL-2,2-DIMETHYL-3-(2,2-DIHALOVINYL)-CYCLOPROPANE-1-CARBOXYLATES

[75] Inventors: Saleem Farooq, Ettingen; Peter Ackermann, Reinach; Jozef Drabek, Oberwil; Laurenz Gsell, Basel; Odd Kristiansen, Möhlin; Rudolf Wehrli, Rheinfelden, all of Switzerland

[73] Assignee: Ciba-Geigy Corporation, Ardsley, N.Y.

[21] Appl. No.: 501,457

[22] Filed: Jun. 6, 1983

Related U.S. Application Data

[63] Continuation-in-part of Ser. No. 216,222, Dec. 9, 1980, abandoned, which is a continuation-in-part of Ser. No. 122,543, Feb. 19, 1980, abandoned, which is a continuation of Ser. No. 049,363, Jun. 18, 1979, abandoned.

[30] Foreign Application Priority Data

Jun. 27, 1978 [CH]  Switzerland ........................ 6990/78
Mar. 19, 1979 [CH]  Switzerland ........................ 2559/79

[51] Int. Cl.$^4$ .................. C07C 69/743; A01N 53/00
[52] U.S. Cl. ..................................... 514/531; 560/124
[58] Field of Search ................ 560/124; 424/305; 514/531

[56] References Cited

U.S. PATENT DOCUMENTS

| | | | |
|---|---|---|---|
| 1,438,129 | 6/1976 | Davis | 560/124 |
| 3,927,068 | 12/1975 | Searle | 560/124 |
| 3,979,424 | 9/1976 | Searle | 560/124 |
| 4,024,163 | 5/1977 | Elliott | 560/124 |

FOREIGN PATENT DOCUMENTS 8332    3/1980  European Pat. Off.
2923217 12/1979 Fed. Rep. of Germany.

OTHER PUBLICATIONS

Mayfield, J. Text, Inst., 70, pp. 53–61 (1979).

*Primary Examiner*—Michael L. Shippen
*Attorney, Agent, or Firm*—Edward McC. Roberts; Bruce M. Collins

[57] ABSTRACT

Prop-1-ynyl-3-phenoxybenzyl-2,2-dimethyl-3-(2',2'-dihalovinyl)-cyclopropane-1-carboxylates of the formula

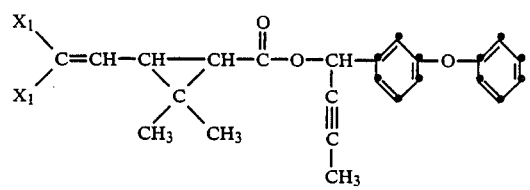

in which $X_1$ if fluorine, chlorine or bromine, and their use in combating pests.

7 Claims, No Drawings

INSECTICIDAL PROP-1-YNYL-3-PHENOXYBENZYL-2,2-DIMETHYL-3-(2,2-DIHALOVINYL)-CYCLOPROPANE-1-CARBOXYLATES

This is a continuation-in-part of our copending application Ser. No. 216,222 filed Dec. 9, 1980 which is in turn a continuation-in-part of application Ser. No. 122,543 filed Feb. 19, 1980, which is a continuation of application Ser. No. 049,363 filed June 18, 1979; all now abandoned.

The present invention relates to prop-1-ynyl-3-phenoxybenzyl-2,2-dimethyl-3-(2',2'-dihalovinyl)-cyclopropane-1-carboxylates, and to their use in combating pests.

The prop-1-ynyl-3-phenoxybenzyl-2,2-dimethyl-3-(2',2'-dihalovinyl)-cyclopropane-1-carboxylates have the formula

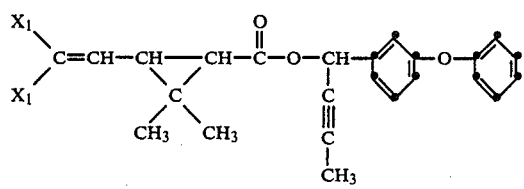

(I)

in which $X_1$ is fluorine, chlorine or bromine.

The compounds of the formula I are produced by methods known per se, for example as follows:

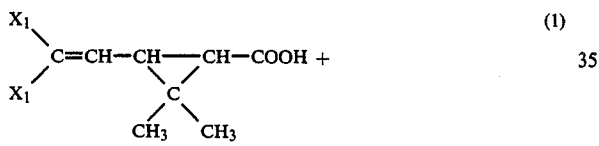

(1)

(II)

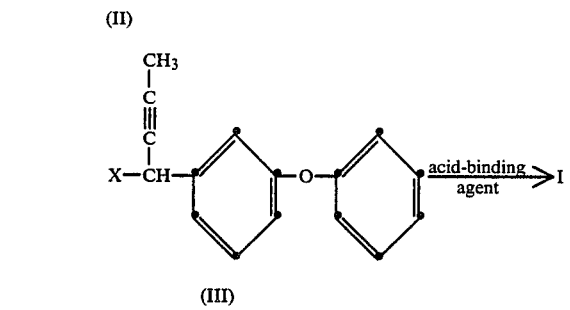

(III)

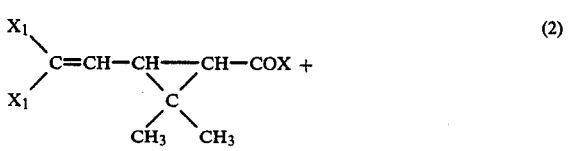

(2)

(IV)

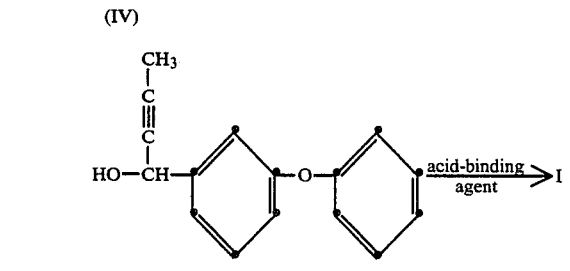

(V)

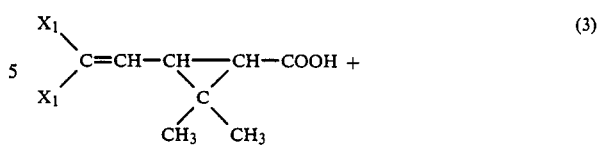

(3)

(II)

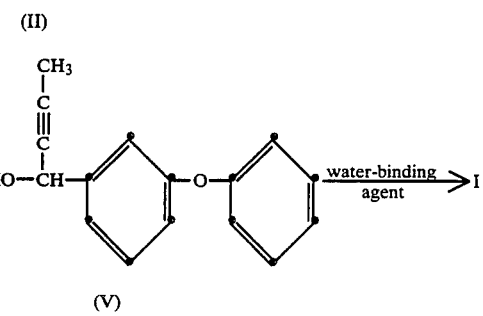

(V)

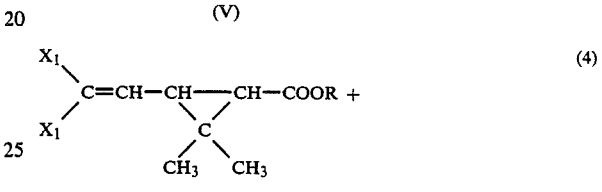

(4)

(VI)

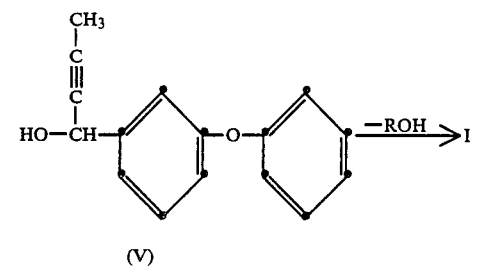

(V)

In the formulae II to VI, the symbol $X_1$ has the meaning given under the formula I.

In the formulae III and IV, X is a halogen atom, particularly chlorine or bromine; and in the formula VI, R is $C_1$–$C_4$-alkyl, especially methyl or ethyl. Suitable acid-binding agents for the processes 1 and 2 are in particular tertiary amines such as trialkylamine and pyridine, also hydroxides, oxides, carbonates and bicarbonates of alkali metals and alkaline-earth metals, as well as alkali metal alcoholates, such as potassium tert-butylate and sodium methylate. The water-binding agent used for process 3 can be, for example, dicyclohexylcarbodiimide. The processes 1 to 4 are performed at a reaction temperature of between $-10°$ and $120°$ C., usually between $20°$ and $80°$ C., under normal or elevated pressure, and preferably in an inert solvent or diluent. Suitable solvents or diluents are for example: ethers and ethereal compounds such as diethyl ether, dipropyl ether, dioxane, dimethoxyethane and tetrahydrofuran; amides such as N,N-dialkylated carboxylic acid amides; aliphatic, aromatic and halogenated hydrocarbons, particularly benzene, toluene, xylenes, chloroform and chlorobenzene, nitriles such as acetonitrile; dimethylsulfoxide, and ketones such as acetone and methyl ethyl ketone.

The starting materials of the formulae II to VI are known, or they can be produced by methods analogous to known methods.

If homogeneous optically active starting materials are not used in producing the compounds of the formula I, these compounds are obtained as mixtures of various optically active isomers. The different isomeric mixtures can be separated by known methods into the individual isomers. It is to be understood that the term 'compounds of the formula I embraces both the individual isomers and the mixtures thereof.

The compounds of the formula I are suitable for combating various animal and plant pests.

The compounds of the formula I are particularly suitable for combating insects, phytopathogenic mites and ticks, for example of the orders: Lepidoptera, Coleoptera, Homoptera, Heteroptera, Diptera, Acarina, Thysanoptera, Orthoptera, Anoplura, Siphonaptera, Mallophaga, Thysanura, Isoptera, Psocoptera and Hymenoptera. The compounds of the formula I are suitable in particular for combating insects that damage plants, especially insects that damage plants by eating, in crops of ornamental plants and useful plants, particularly in cotton crops (for example against *Spodoptera littoralis* and *Heliothis virescens*), and in crops of vegetables (for example against *Leptinotarsa decemlineata* and *Myzus persicae*). Active substances of the formula I have a very good action also against flies, such as *Musca domestica*, and against mosquito larvae.

Compounds of the formula I surprisingly have an insecticidal and acaricidal spectrum of activity broader than that of analogous compounds known from the British patent application No. 1,438,129.

Since compounds of formula I have a lower toxicity to fish than the compound of formula

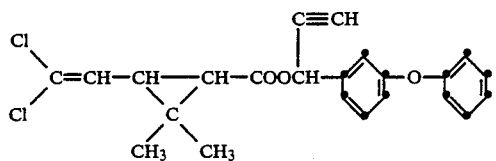

known from the British patent application No. 1,438,129, they may in addition be used to control rice pests, e.g. *Chilo suppressalis,* in rice paddies wherein fish are kept.

The acaricidal and insecticidal action can be substantially broadened and adapted to suit given circumstances by the addition of other insecticides and/or acaricides. Suitable additives are for example: organic phosphorus compounds, nitrophenols and derivatives thereof, formamidines, ureas, other pyrethrin-like compounds, and also carbamates and chlorinated hydrocarbons.

Compounds of the formula I are combined particularly advantageously also with substances which have a synergistic or intensifying effect on pyrethroids. Examples of such compounds are, inter alia, piperonylbutoxide, pyropynyl ethers, propynyl oximes, propynyl carbamates and propynyl phosphonates, 2-(3,4-methylenedioxyphenoxy)-3,6,9-trioxaundecane (Sesamex or Sesoxane), S,S,S-tributylphosphorotrithioates and 1,2-methylenedioxy-4-(2-(octylsulfinyl)-propyl)-benzene.

The compounds of the formula I possess also an activity against insects that feed on keratin, for example against Lepidoptera such as Tineola spec. and Tinea spec., and against Coleoptera, for example Anthrenus spec., and Attagenus spec. The active substances of the formula I are therefore suitable for proofing keratinous materials, for example raw or processed sheep's wool, products made of other animal hairs, hides, furs and feathers, against feeding damage by insects.

The compounds of the formula I are applied to the above substrates, in particular woollen textiles and wool blends, preferably by methods commonly known and employed in dyeing, such as the exhaust method and padding.

The amount of active substance of the formula (I) employed depends on the respective substrate and on the method of application. However, it is normally such that, after application to the material to be protected, the latter contains about 10 to 2000 ppm, preferably 200 to 1000 ppm, of active substance. This corresponds, for example, to concentrations of 0.005 to 1 g/l of treatment bath, depending on the degree of exhaustion, in the exhaust method at a liquor ratio of 1:20. In the pad method, concentrations of up to 2 g/l are possible.

Compounds of the formula I can be used on their own or together with suitable carriers and/or additives. Suitable additives can be solid or liquid and they correspond to the substances common in formulation practice, such as natural or regenerated substances, solvents, dispersing agents, wetting agents, adhesives, thickeners, binders and/or fertilisers.

The compositions according to the invention are produced in a manner known per se by the intimate mixing and/or grinding of the active substances of the formula I with suitable carriers, optionally with the addition of dispersing agents or solvents which are inert to the active substances. The active ingredients may be processed to the following formulations:

solid formulations:
dusts, scattering agents, granules (coated granules, impregnated granules and homogeneous granules);
liquid formulations:
(a) water-dispersible concentrates of active substance: wettable powders, pastes or emulsions;
(b) solutions.

The content of active substance in the compositions described is between 0.1 and 95%; it is to be mentioned in this respect that with application from an aeroplane, or from other suitable devices, concentrations of up to 99.5% or even the pure active substance can be used.

The active substances of the formula I can be formulated for example as follows (parts are by weight):
Dusts
The following substances are used to produce
(a) a 5% dust and
(b) a 2% dust:
(a) 5 parts of active substance, and 95 parts of talcum;
(b) 2 parts of active substance, 1 part of highly dispersed silicic acid, and 97 parts of talcum.

The active substance is mixed and ground with the carriers.
Granulate
The following ingredients are used to produce a 5% granulate:
5 parts of active substance,
0.25 parts of epoxidised vegetable oil,
0.25 parts of cetyl polyglycol ether,
3.50 parts of polyethylene glycol, and
91 parts of kaolin (particle size 0.3–0.8 mm).

The active substance is mixed with epoxidised vegetable oil, and dissolved in 6 parts of acetone; the polyethylene glycol and cetyl polyglycol ether are then added. The solution thus obtained is sprayed onto kaolin, and the acetone is subsequently evaporated off in vacuo.

Wettable powders

The following constituents are used to produce (a) a 40% wettable powder, (b) and (c) a 25% wettable powder and (d) a 10% wettable powder:

(a)
  40 parts of active substance,
  5 parts of sodium lignin sulfonate,
  1 part of sodium dibutyl-naphthalene sulfonate, and
  54 parts of silicic acid;

(b)
  25 parts of active substance,
  4.5 parts of calcium lignin sulfonate,
  1.9 parts of champagne chalk/hydroxyethyl cellulose mixture (1:1),
  1.5 parts of sodium dibutyl-naphthalene sulfonate,
  19.5 parts of silicic acid,
  19.5 parts of champagne chalk, and
  28.1 parts of kaolin;

(c)
  25 parts of active substance,
  2.5 parts of isooctylphenoxy-polyoxyethyleneethanol,
  1.7 parts of champagne chalk/hydroxyethyl cellulose mixture (1:1),
  8.3 parts of sodium aluminium silicate,
  16.5 parts of kieselguhr, and
  46 parts of kaolin; and (d)
  10 parts of active substance,
  3 parts of a mixture of the sodium salts of saturated fatty alcohol sulfates,
  5 parts of naphthalenesulfonic acid/formaldehyde condensate, and
  82 parts of kaolin.

The active substance is intimately mixed in suitable mixers with the additives, and the mixture is then ground in the appropriate mills and rollers to obtain wettable powders which can be diluted with water to give suspensions of the concentration desired.

Emulsifiable concentrates

The following substances are used to produce (a) a 10% emulsifiable concentrate, (b) a 25% emulsifiable concentrate and (c) a 50% emulsifiable concentrate:

(a)
  10 parts of active substance,
  3.4 parts of epoxidised vegetable oil,
  3.4 parts of a combination emulsifier consisting of fatty alcohol polyglycol ether and alkylarylsulfonate calcium salt,
  40 parts of dimethylformamide, and
  43.2 parts of xylene;

(b)
  25 parts of active substance,
  2.5 parts of epoxidised vegetable oil,
  10 parts of alkylarylsulfonate/fatty alcohol polyglycol ether mixture,
  5 parts of dimethylformamide, and
  57.5 parts of xylene; and (c)
  50 parts of active substance,
  4.2 parts of tributylphenylpolyglycol ether,
  5.8 parts of calcium-dodecylbenzenesulfonate,
  20 parts of cyclohexanone, and
  20 parts of xylene.

Emulsions of the required concentration can be prepared from these concentrates by dilution with water.

Sprays

The following constituents are used to produce (a) a 5% spray and (b) a 95% spray:

(a)
  5 parts of active substance,
  1 part of epoxidised vegetable oil,
  94 parts of ligroin (boiling limits 160°–190° C.);

(b)
  95 parts of active substance, and
  5 parts of epoxidised vegetable oil.

The invention is further illustrated by the Examples which follow.

EXAMPLE 1

(a) Production of α-prop-1-ynyl-3-phenoxybenzyl alcohol

A Grignard solution, freshly prepared from 4 g of magnesium and 20 g of ethyl bromide in 20 ml of tetrahydrofuran, is slowly added at 0° C. to a solution of 8 g of methylacetylene in 100 ml of tetrahydrofuran, and the mixture is stirred under argon for 15 minutes. There is then added dropwise to this mixture at 0° to 5° C. a solution of 27 g of o-phenoxybenzaldehyde in 100 ml of tetrahydrofuran. After being stirred for 14 hours at room temperature, the reaction mixture is cooled to 0° C. with 50 g of ice; 25 ml of conc. hydrochloric acid is subsequently slowly added, and extraction is performed with ether. The ether extract is washed twice with water and twice with saturated sodium chloride solution; it is then dried over sodium sulfate, filtered, and concentrated by evaporation. The product is chromatographed through silica gel with ethyl acetate/hexane (1:1) as the eluant. There is thus obtained the compound of the formula

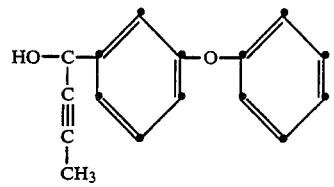

having a refractive index of $n_D^{20} = 1.5898$.

(b) Production of α-prop-1-ynyl-3-phenoxybenzyl-2,2-dimethyl-3-(2'2'-dichlorovinyl)-cyclopropane-1-carboxylate A solution of 4 g of α-prop-1-ynyl-3-phenoxybenzyl alcohol in 20 ml of toluene is added dropwise to an ice-cooled solution of 3.82 g of 2,2-dimethyl-3-(2',2'-dichlorovinyl)-cyclopropanecarboxylic acid chloride and 1.8 ml of pyridine in 50 ml of toluene. The reaction mixture is stirred for 14 hours at room temperature, and ether is then added. The ether extract is washed once with water, once with 2N hydrochloric acid and three times with a saturated sodium chloride solution; it is subsequently dried over sodium sulfate, filtered, and concentrated by evaporation. The product is chromatographed through silica gel with ether/hexane (1:3) as the eluant. There is thus obtained the compound of the formula

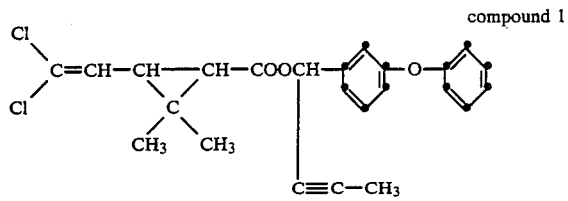

compound 1 as a diastereoisomeric mixture having a refractive index of $n_D^{20} = 1.5700$.

The following compounds are produced in an analogous manner:

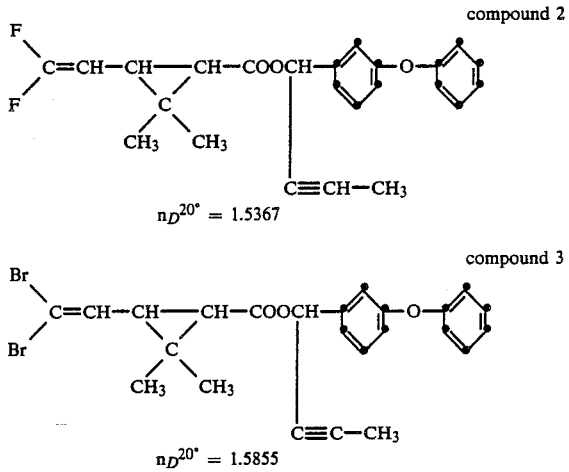

compound 2, $n_D^{20°} = 1.5367$ compound 3, $n_D^{20°} = 1.5855$

EXAMPLE 2

(a) Insecticidal stomach-poison action

Cotton plants were sprayed with a 0.05% aqueous active substance solution (obtained from a 10% emulsifiable concentrate). After drying of the coating, larvae of *Spodoptera littoralis* in the L₃-stage and of *Heliothis virescens* in the L₃-stage were placed onto the cotton plants. The test was carried out at 24° C. with 60% relative humidity.

Compounds according to Example (1b) exhibited in the above test a good insecticidal stomach-poison action against *Spodoptera littoralis* and *Heliothis virescens* larvae.

EXAMPLE 3

Acaricidal action

*Phaseolus vulgaris* plants were infested, 12 hours before the test for acaricidal action, with an infested piece of leaf from a mass culture of *Tetranychus urticae*. The transferred mobile stages were sprayed with the emulsified test preparations from a chromatography-sprayer in a manner ensuring no overflow of the spray-liquor. An assessment was made after 2 and 7 days, by examination under a binocular microscope, of the living larvae and of the dead larvae, adults and eggs, and the results were expressed as percentages. The treated plants were kept during the "holding time" in greenhouse compartments at 25° C.

Compounds according to Example (1b) were effective in the above test against adults, larvae and eggs of *Tetranychus urticae*.

EXAMPLE 4

Action against ticks (a) *Rhipicephalus bursa*

For each concentration, 5 adult ticks and 50 tick larvae, respectively, were counted into a small glass test tube, and immersed for 1 to 2 minutes in 2 ml of an aqueous emulsion from a dilution series of 100, 10, 1 and 0.1 ppm of test substance. The tubes were then sealed with a standardised cotton plug, and inverted so that the active substance emulsion could be absorbed by the cotton wool.

The evaluation in the case of the adults was made after 2 weeks and in the case of the larvae after 2 days. There were two repeats for each test.

(b) *Boophilus microplus* (larvae)

With a dilution series analogous to that of Test (a), tests were carried out with 20 sensitive larvae and OP-resistant larvae, respectively (resistance is with respect to diazinon compatibility).

Compounds according to Example (1b) were effective in these tests against adults and larvae of *Rhipicephalus bursa* and against sensitive and OP-resistant larvae, respectively, of *Boophilus microplus*.

EXAMPLE 5

Toxicity to fish: Comparison test

Test compounds

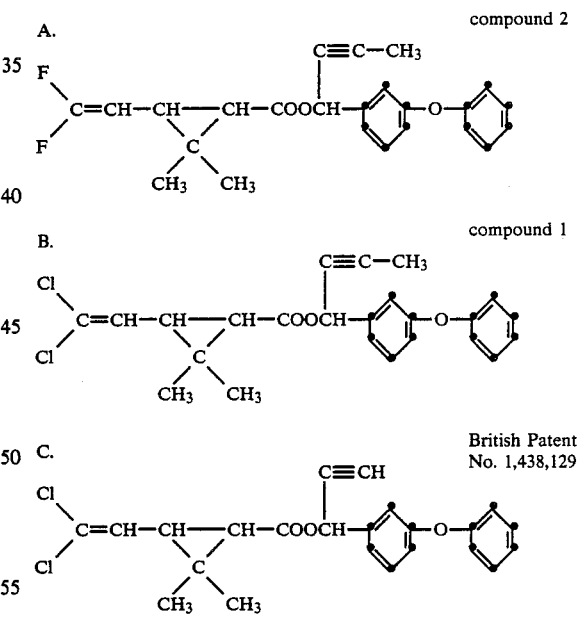

A. compound 2

B. compound 1

C. British Patent No. 1,438,129

Part I

Test animal

*Brachydanio rerio* (zebra-barbel fish).

Test

4 Zebra-barbel fish 2 cm in length (*Brachydanio rerio*) were put into 10 l of water at a temperature of 24° C. After three days 0.01 mg; 0.1 mg; 1 mg and 10 mg of test substance, dissolved in 10 ml of acetone, were added. A mortality count was made after 24 and 96 hours.

Test results

% mortality of *Brachydanio rerio* with a 1 ppm; 0.1 ppm; 0.01 ppm and 0.001 ppm aqueous preparation of test compound.

|  | After 96 hours | | | |
|---|---|---|---|---|
|  | 1 ppm | 0.1 ppm | 0.01 ppm | 0.001 ppm |
| Compound A | 0 | 0 | 0 | 0 |
| Compound B | 0 | 0 | 0 | 0 |
| Compound C | 100 | 100 (also 100 after 24 hours) | 50 | 0 |

1 ppm = 10 mg active substance per 10 l of water
0.1 ppm = 1 mg active substance per 10 l of water
0.01 ppm = 0.1 mg active substance per 10 l of water
0.001 ppm = 0.01 mg active substance per 10 l of water Conclusion Compounds A and B have no toxicity to the fish *Brachydanio rerio* at 1 ppm, whereas compound C is highly toxic at the concentration of 0.01 ppm to this fish, and has no toxicity at the concentration of 0.001 ppm.

Part II

Test animal
  *Nilaparvata lugens*. Brown rice planthopper.
Test preparation
  Emulsifiable concentrate
  10 parts of active substance,
  3.4 parts of epoxidised vegetable oil,
  3.4 parts of combination emulsifier consisting of fatty alcohol polyglycol ether and alkylarylsulfate, calcium salt,
  40 parts of dimethylformamide, and
  43.2 parts of xylene.
Test Preparations having concentrations of 50 and 100 ppm of active substance (prepared from the test preparation by addition of water) were sprayed onto rice plants grown for 1 month in plastic cups having a capacity of 180 ml, which were placed on a revolving table. The application rate was 50 ml/2 cups. After air drying, the plants were covered with wire netting cages. 10 third instar larvae of *Nilaparvata lugens* were put into each cage. The cages were kept in an artificial climate chamber maintained at 22° C. After 24 hours, the numbers of living and killed larvae were determined. Each test was conducted eight times.

| Test results | | |
|---|---|---|
| % mortality of *Nilaparvata lugens* larvae | | |
|  | 100 | 50 ppm active substance |
| Compound A | 65 | 60 |
| Compound B | 60 | 55 |
| Compound C | 80 | 65 |

Conclusion

At a concentration of 50 ppm and 100 ppm the test compounds A, B and C have approximately the same activity against larvae of *Nilaparvata lugens*.
Fish-toxicity safety coefficient The fish-toxicity safety coefficient was calculated from data obtained in the fish-toxicity and insecticidal tests according to the following formula $$\text{fish-toxicity safety coefficient} = \frac{\text{fish-toxicity}}{\text{insecticidal activity } (LD\ 50)}$$

In the case of *Nilaparvata lugens*, the preparations of compounds A and B having a concentration corresponding to the LD 50 values (compound A of 40 ppm; compound C of 30 ppm and compound B of 45 ppm calculated from the activity data against *Nilaparvata lugens*) at the time of spraying were sprayed onto a paddy field, having a water depth of 5 cm, at a rate of 100 l per 100 m$^2$, and the concentration in water was determined on the basis of the assumption that all the preparation had gone into the water. Since the amount of water in the paddy field of 1000 m$^2$ having a depth of 5 cm is 50 tons, and if the chemical solutions of compounds A; B and C are applied at a rate of 100 l per 1000 m$^2$ at an effective active substance concentration corresponding to the LD 50 values (compound A=40 ppm; compound B=45 ppm and compound C=30 ppm), the active substance concentration in water is 0.08 ppm (compound A); 0.09 ppm (compound B) or 0.06 ppm (compound C)

$$\text{fish-toxicity safety coefficient of compound } A = \frac{1}{0,08} = 12,5$$

$$\text{fish-toxicity safety coefficient of compound } B = \frac{1}{0,09} = 11,1$$

$$\text{fish-toxicity safety coefficient of compound } C = \frac{0,001}{0,06} = 0,0167$$

Conclusion

Compound A and B have very low toxicity to fish and may be used therefore to combat insecticidal rice pests in paddy rice fields where fish are bred, whereas compound C, on account of the very low fish-toxicity safety coefficient is unsuitable for combating insecticidal pests in such paddy rice fields.

EXAMPLE 6

Mothproofing test (exhaust method)

A 0.4% stock solution of each of the compounds of example 1b in ethylene glycol monomethyl ether is prepared. An aqueous treatment bath containing, in 120 ml of distilled water, 0.12 ml of a wetting agent and dispersant, 0.6 ml of formic acid 1:10 and 0.75 ml of the respective 0.4% stock solution is then prepared at room temperature, and 3 g of wool flannel are wetted with hot water and put into the bath at room temperature. With constant circulation of the wool sample, the bath temperature is raised to 60° C. in the course of 20 minutes and treatment is carried out for 30 minutes at 60° C. The bath is subsequently cooled; the wool sample is then rinsed twice for 3 minutes with distilled water, squeezed out by hand and dried in air. The active substance concentration is 1000 ppm, based on the weight of the wool.

The dried sample is subjected to the mothproofing test (protection against feeding damage caused by the webbing clothes moth *Tineola biselliella* Hum.), in accordance ith SNV 195901, and to the test against larvae of the fur beetle (*Attagenus piceus* Ol) and carpet beetle (*Anthrenus vorax* Wat.) in accordance with SNV 195902. In these tests, larvae of Attagenus and 6- to 7-week-old larvae of *Attagenus piceus* are used. Pieces of the same size are cut out of the treated wool samples and subjected for 14 days at constant temperature (28° C.) and constant relative humidity (65%) to attack (feeding) by 15 larvae of each of the pests. Evaluation is made on the one hand according to the relative loss in weight of the test sample and, on the other, according to the number of still living organisms.

The tested compounds of example 1b exhibit very good action against the three pests.

EXAMPLE 7

Mothproofing test (pad method)

A 0.4% stock solution of each of the compounds of example 1b in ethylene glycol monomethyl ether is prepared. Each of the stock solutions (12.5 ml) is diluted to 50 ml (solution 1) with glycol monomethyl ether which contains 0.65 g/l of a wetting agent and dispersant. Solution 1 (25 ml) is diluted to 50 ml (solution 2) with glycol monomethyl ether which contains 0.5 g/l of a wetting agent and dispersant. Solution 2 (25 ml) is diluted in its turn to 50 ml (solution 3) with glycol monomethyl ether which contains 0.5 g/l of a wetting agent and dispersant;

3 ml of each of solutions 1, 2 and 3 are poured into crystallisation dishes and a disc of wool flannel is wetted for 3 seconds therein. The moist discs are then padded between aluminium sheets to give a pickup of 50% of each solution. The concentrations of active substance are, respectively, 500 ppm, 250 ppm and 125 ppm for the discs treated with solutions 1, 2 and 3. The discs are then dried in air and subjected to the same biological tests as in Example 1.

The tested compounds of example 1b exhibit very good action against all 3 pests, even at the lowest concentration of 125 ppm.

What is claimed is:

1. A cyclopropanecarboxylic acid ester of the formula $$\underset{X_1}{\overset{X_1}{\diagdown}}C=CH-CH\underset{\underset{CH_3}{|}}{\overset{}{\diagdown}}\underset{\overset{}{C}\diagdown CH_3}{\diagup}CH-\overset{O}{\overset{\|}{C}}-O-CH\underset{\underset{\underset{CH_3}{|}}{\overset{}{C}}}{\overset{}{\underset{\|}{\overset{}{C}}}}\diagdown\phantom{-}\underset{\phantom{-}}{\phantom{-}}-O-\phantom{-}\underset{\phantom{-}}{\phantom{-}}$$

in which $X_1$ is fluorine, chlorine or bromine.

2. The compound according to claim 1 of the formula $$\underset{F}{\overset{F}{\diagdown}}C=CH-CH\diagdown\underset{\underset{CH_3}{|}}{\overset{}{C}}\diagup CH-COOCH\underset{\underset{\underset{CH_3}{|}}{\overset{}{C}}}{\overset{}{\underset{\|}{\overset{}{C}}}}\diagdown\phantom{-}-O-\phantom{-}.$$

3. The compound according to claim 1 of the formula $$\underset{Br}{\overset{Br}{\diagdown}}C=CH-CH\diagdown\underset{\underset{CH_3}{|}}{\overset{}{C}}\diagup CH-COOCH\underset{\underset{\underset{CH_3}{|}}{\overset{}{C}}}{\overset{}{\underset{\|}{\overset{}{C}}}}\diagdown\phantom{-}-O-\phantom{-}.$$

4. The compound according to claim 1 of the formula $$\underset{Cl}{\overset{Cl}{\diagdown}}C=CH-CH\diagdown\underset{\underset{CH_3}{|}}{\overset{}{C}}\diagup CH-COOCH\underset{\underset{\underset{CH_3}{|}}{\overset{}{C}}}{\overset{}{\underset{\|}{\overset{}{C}}}}\diagdown\phantom{-}-O-\phantom{-}.$$

5. An insecticidal composition which comprises an insecticidally effective compound according to claim 1 as active ingredient, and suitable carriers.

6. A method of combating insects at a locus which comprises applying to said locus an insecticidally effective amount of a compound of the formula $$\underset{X_1}{\overset{X_1}{\diagdown}}C=CH-CH\diagdown\underset{\underset{CH_3}{|}}{\overset{}{C}}\diagup CH-\overset{O}{\overset{\|}{C}}-O-CH\underset{\underset{\underset{CH_3}{|}}{\overset{}{C}}}{\overset{}{\underset{\|}{\overset{}{C}}}}\diagdown\phantom{-}-O-\phantom{-}$$

in which $X_1$ is fluorine, chlorine or bromine.

7. A method according to claim 6 in which rice plants are protected.

* * * * *